US009883986B2

(12) United States Patent
Mochizuki et al.

(10) Patent No.: US 9,883,986 B2
(45) Date of Patent: Feb. 6, 2018

(54) STANDING BAG TYPE INFUSION LIQUID CONTAINER

(71) Applicant: EA Pharma Co., Ltd., Chuo-ku (JP)

(72) Inventors: Shota Mochizuki, Shizuoka (JP); Naoki Morinaka, Shizuoka (JP)

(73) Assignee: EA Pharma Co., Ltd., Chuo-ku (JP)

( * ) Notice: Subject to any disclaimer, the term of this patent is extended or adjusted under 35 U.S.C. 154(b) by 1042 days.

(21) Appl. No.: 14/155,420

(22) Filed: Jan. 15, 2014

(65) Prior Publication Data
US 2014/0126843 A1 May 8, 2014

Related U.S. Application Data

(63) Continuation of application No. PCT/JP2012/076268, filed on Oct. 11, 2012.

(30) Foreign Application Priority Data

Oct. 11, 2011 (JP) .................................. 2011-223843

(51) Int. Cl.
*A61B 19/00* (2006.01)
*A61J 1/10* (2006.01)
(Continued)

(52) U.S. Cl.
CPC ................ *A61J 1/10* (2013.01); *A61J 1/1462* (2013.01); *A61J 1/1493* (2013.01); *B65B 3/003* (2013.01);
(Continued)

(58) Field of Classification Search
CPC A61J 1/10; A61J 1/1462; A61J 1/1493; A61J 2200/76; B65B 3/003; B65B 55/022;
(Continued)

(56) References Cited

U.S. PATENT DOCUMENTS 3,208,710 A * 9/1965 Barton ..................... A61J 1/05
220/606
3,215,299 A * 11/1965 Coanda .................... A61J 1/05
215/232
(Continued)

FOREIGN PATENT DOCUMENTS

JP 02-092529 A 4/1990
JP 04-067450 U 6/1992
(Continued)

OTHER PUBLICATIONS

International Search Report issued Jan. 22, 2013 in Application No. PCT/JP2012/076268, filed Oct. 11, 2012.

*Primary Examiner* — Tatyana Zalukaeva
*Assistant Examiner* — Andrew J Mensh
(74) *Attorney, Agent, or Firm* — Oblon, McClelland, Maier & Neustadt, L.L.P.

(57) ABSTRACT

The present invention relates to a standing bag type container and aims to increase a visibility of the residual liquid volume in accordance with the progress of infusion process. The standing bag type container includes a bag 10 made of soft resin films and forming at its one end a base member 20 and an outlet port 18 at the other end of the bag. A suspension of the bag 10 is done in a manner that the base member 20 is located at the top. Marks for indication of residual liquid volume are printed on the surface of the bag. An infusion liquid is charged to the bag while an air gap 109' is left, so that a residual liquid volume is verified from the liquid level. Under the suspended condition, the base member 20 has a value of width which is unchanged from the when the bag is under upright condition. The base member 20 is not collapsed and maintains its width even when the residual liquid volume is zero. A portion of the bag of a predetermined height from the top edge of the bag including (Continued)

the base member 20 maintains its shape without being collapsed by a discharge of the liquid.

9 Claims, 14 Drawing Sheets

(51) Int. Cl.
| | | |
|---|---|---|
| *B65B 3/00* | (2006.01) | |
| *B65B 55/02* | (2006.01) | |
| *A61J 1/14* | (2006.01) | |
| *A61M 1/16* | (2006.01) | |
| *A61M 25/00* | (2006.01) | |

(52) U.S. Cl.
CPC ......... *B65B 55/022* (2013.01); *A61J 2200/76* (2013.01); *A61M 1/1601* (2014.02); *A61M 2025/0059* (2013.01); *A61M 2205/3334* (2013.01); *F04C 2270/0421* (2013.01)

(58) Field of Classification Search
CPC ... F04C 2270/0421; A61M 2205/3334; A61M 1/1601; A61M 2025/0059

USPC ................ 604/403, 404, 405, 406, 407, 408
See application file for complete search history.

(56) References Cited

U.S. PATENT DOCUMENTS

| 4,100,953 A * | 7/1978 | Miller ..................... A61J 1/10 |
| | | 222/107 |
| 4,911,708 A * | 3/1990 | Maezaki .................. A61J 1/05 |
| | | 215/DIG. 3 |
| 2005/0059951 A1* | 3/2005 | Young .................. A61F 5/4405 |
| | | 604/403 |

FOREIGN PATENT DOCUMENTS

| JP | 05-007641 U | 2/1993 |
| JP | 3554418 B2 | 8/2004 |
| JP | 2005-271974 A | 10/2005 |

* cited by examiner

Prior Art

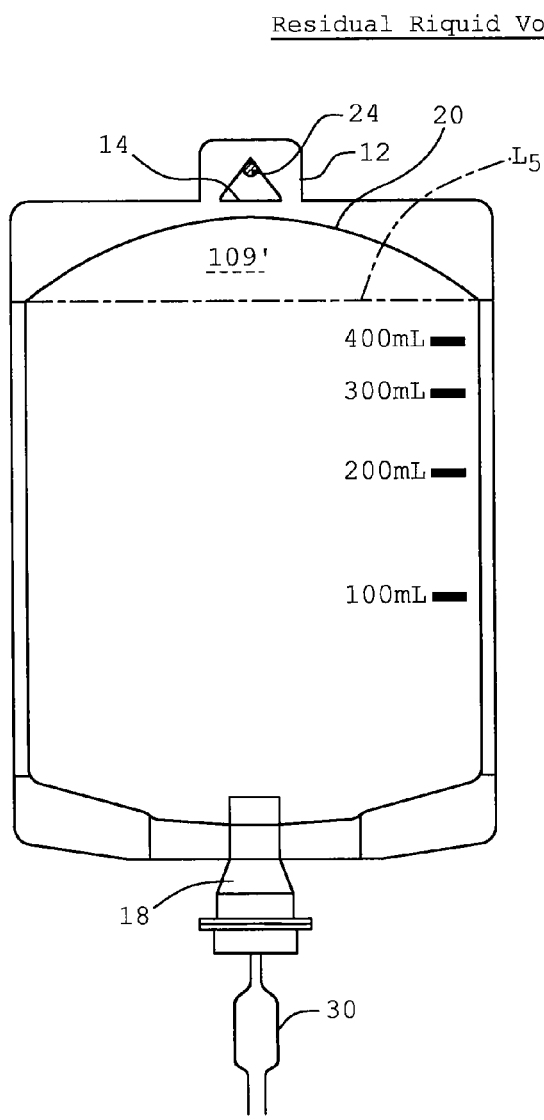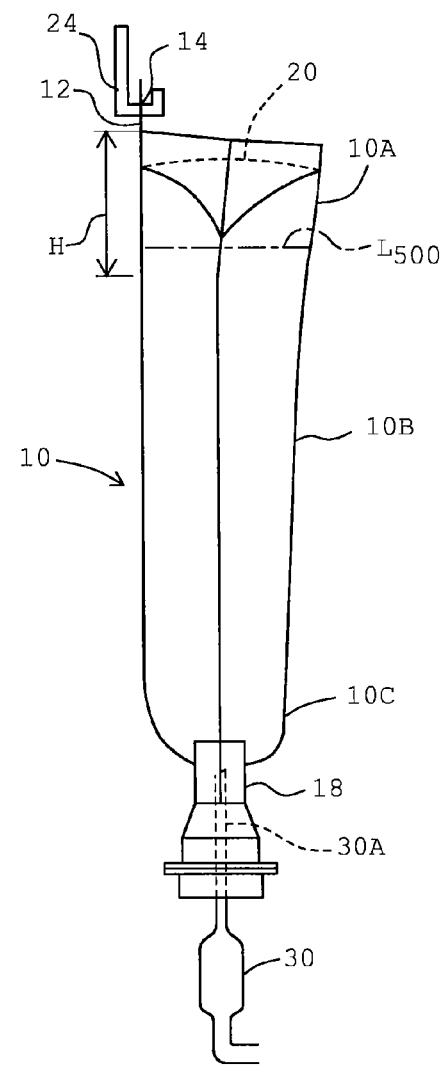

Fig.12(A)
Fig.12(B)
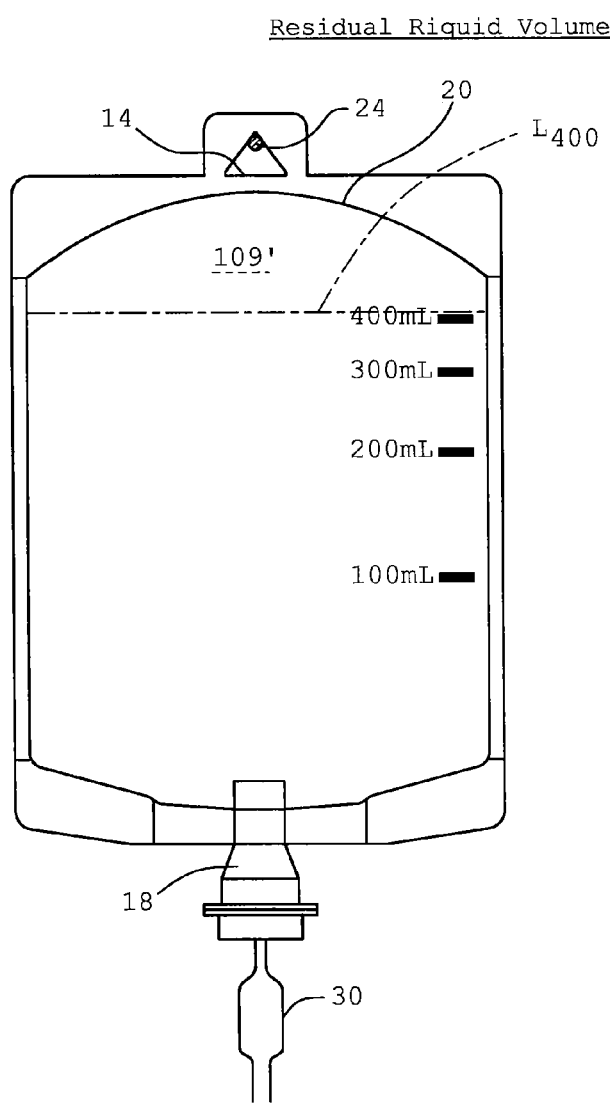
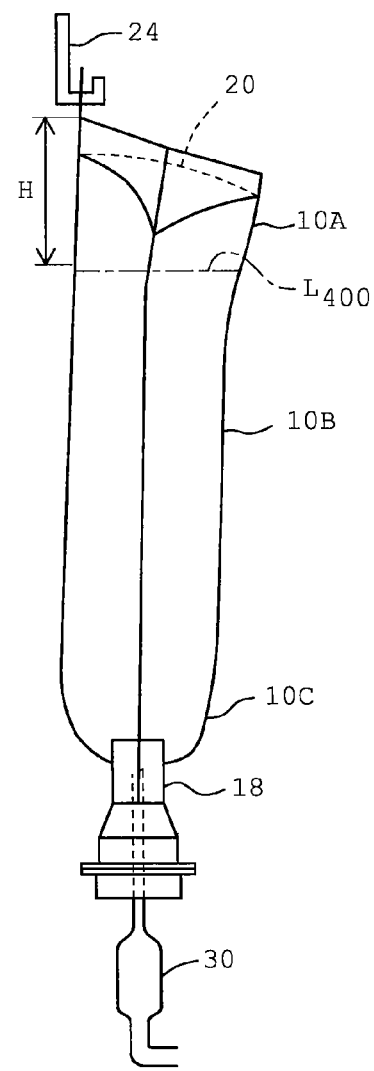

STANDING BAG TYPE INFUSION LIQUID CONTAINER

TECHNICAL FIELD

The present invention relates to a standing bag type infusion liquid container, having a flat bag made from soft films, of which material is polyolefin-based resin, capable of obtaining an increased visibility concerning an indicated degree of residual liquid volume in accordance with progress of an infusion process.

BACKGROUND TECHNOLOGY

An infusion bag forms usually a shape of flat pouch, which is inconvenient in a pre-setup operation, such as a mixing injection et al, to be executed prior to the commencement of an infusion operation. In view of this, an infusion bag of a standing bag type has heretofore been proposed. Such an infusion bag of standing bag type has, at its one end, a base member, whereat the thickness of the bag is correspondingly increased, thereby allowing the bag to obtain a self-standing capability. A pre-setup operation, such as mixing injection, becomes thus possible at a self-standing state of the bag. Such a standing bag type infusion liquid container is, at a part of the base member, provided with an engaging part (an opening) for allowing the container to be suspended from an infusion stand for executing an infusion operation. As similar to an infusion process in the flat pouch type, a progress of a discharge of the infusion liquid from an infusion liquid container of the standing bag type is made possible by a progress of a collapse of the bag. As similar to the flat pouch type, the infusion liquid container of the standing bag type is collapsed also at the base end evenly as the remaining part thereof for obtaining an entirely compacted shape of the bag when disposed. See Patent Documents 1 and 2.

PRIOR TECHNOLOGY DOCUMENTS

Patent Documents

Patent Document 1: Japanese Un-Examined Utility Model Publication No. H5-7641
Patent Document 2: Japanese Examined Patent Publication No.

SUMMARY OF THE INVENTION

Problems to be Solved by the Invention

In the standing bag type infusion liquid container in the Patent Documents 1 and 2, a discharge of the liquid is progressed by collapsing evenly and entirely the bag as similar to the infusion liquid container of the flat pouch type. Namely, in the entirely collapsed conventional standing bag type infusion liquid container, the bag is collapsed not only at the body part but also at the bottom part. This collapsing system is advantageous in its increased visibility when an infusion operation is started. The softness of the basic material however causes the opposed film surfaces to be contacted at the body portion of the bag when volume of the residual liquid is reduced to a value around 100 mL, resulting in a discontinuity in the liquid level, which makes the visibility of residual liquid volume to be worsened. A need of improvement in the visibility has, thus, been existed. In many cases, infusion bags have values of storage volume in a range between 200 mL and 500 mL. Specially, in case of an infusion by a drip to a patient by using an infusion bag of a value of volume of 500 mL, a nurse makes rounds to learn the residual volume of the liquid and estimates the finishing time not from the scale value at the start but from the residual volume in the range between 100 mL and 200 mL closer to the finishing time. Incidentally, in case of an infusion liquid container of a bottle shape type, which has conventionally been used, a high visibility of the residual volume is obtained not only at the state when an infusion is started but also at the state where the residual volume is equal to or lower than 200 mL due to the fact that the bottle shape is kept, which makes the border of the liquid level to be highly visible.

In view of the above difficulties, the present invention aims to provide an improved standing bag type infusion liquid container, capable of obtaining an increased visibility at a state of a small residual volume of the liquid, which is comparable with the infusion liquid container of the bottle type.

Means for Solving Problem

In the present invention, a standing bag type infusion liquid container comprises: a bag for storing therein with an infusion liquid, the bag being formed from soft films made from a resin material and having an end functioning as a base member; suspension means for suspending the bag in a manner that the base member is located at the top; an outlet port of the infusion liquid at the other end of the bag; and marks for a visual indication of the residual liquid volume, the marks being formed on a surface of the bag. The infusion liquid is filled in the bag such that an air space is left therein for allowing the residual liquid volume to be visible from the liquid level. The base member of the bag under the suspended condition by the suspension means has a value of width, which is equal to or substantially equal to the value of the width under the standing condition of the bag. The base member maintains or substantially maintains its width without being collapsed regardless the discharge of the infusion liquid. Furthermore, the portion of the bag including the base member in a part of the bag of a predetermined height from the top end of the bag constructs a shape retainer for retaining or substantially retaining the width of the part of the bag by preventing the part of the bag from being collapsed regardless the discharge of the liquid.

The suspending means for suspending the infusion liquid container to an infusion stand is formed as an opening on one side of the bag at its top end. In this case, the marks for a visual indication of the residual liquid volume are formed on the other side of the bag.

As a resin film constructing a bag in the present invention, a polyethylene based resin, in particular, a polyethylene resin film is preferable, although there is no intension to exclude other resins such as polypropylene resin. The polyethylene resin film has, in a raw sheet condition, a value of thickness in a range between 180 and 350 μm, preferably 220 and 320 μm. The polyethylene resin film constructing the bag has a value of 1% elastic modulus in tension in a range between 150 and 320 Mpa, preferably in a range between 170 and 280 Mpa.

In order to allow the liquid level to be visible, a space for an air in the bag is provided. In case of a medicine, which is unstable to the oxygen, an inactive gas may preferably be mixed with the air.

In case where a polyethylene material is used, in order to produce a standing bag type infusion liquid container from a raw polyethylene sheet with gusset shaped part, the raw polyethylene sheet is doubled, which closed side is folded inwardly so as to form a gusset shaped portion. The opposed parts of the sheet is welded in a non-separable manner. During the welding, a base part of the bag is formed on the side of the sheet folded to the gusset shape, on one hand and, on the other hand, the opposed surfaces at the opened side of the doubled sheet are partly non-welded so as to leave an opening. An individual bag is cut from the sheet, to which cut bag an outlet port is connected and an infusion liquid is introduced while a desired volume of air space is left, followed by a sealing, thereby constructing a standing bag type infusion container. Then, an sterilizing operation under a wet heat condition is done in a manner that the polyethylene film constructing the bag after the sterilizing operation has a value of 1% elastic modulus in tension is in a range between 150 and 320 Mpa, preferably in a range between 170 and 280 Mpa.

Effects of the Invention

In the standing bag type infusion container in the present invention, the container is suspended by an infusion stand et al in a manner that the base member is at the top in order to effect an infusion operation. The base member does not collapse and maintains its width irrespective of the discharge of the liquid. Furthermore, the portion of the bag including the base member, of a predetermined height from the top edge of the bag retains the shape without being collapsed regardless the liquid discharge. In other words, the bag in the infusion liquid container in the present invention is provided with a structure like a conventional soft bottle type infusion container. As a continuation of the retainer part, the body part of the bag retains, therefore, its opposed surfaces to be separated until the substantial final phase of the infusion process, thereby obtaining a desirably increased visibility of the residual liquid volume.

In order to obtain such a collapsing characteristic of the bag during the progress of the liquid discharge, a suitable control of the rigidity of a raw resin film constructing the bag is important. In case of polyethylene, such a control is obtained by a thickness of the raw film in a range between 180 and 350 µm, preferably between 220 and 320 µm as well as a value of 1% elastic modulus in tension is in a range between 150 and 320 Mpa, preferably, between 170 and 280 Mpa after subjected to a sterilizing operation. Namely, such a sterilizing operation is carried out during a heating under a sealingly stored condition. The sterilization of wet condition by vapor is done for obtaining an increased efficiency and employs a temperature exceeding slightly 100° C. Furthermore, the pressure of the heated vapor causes the bag to be strongly inflated due to the increased volume of the air space, so that the resin film constructing the bag is subjected to a strong degree of stretching. During a cooling phase of the bag after the completion of the sterilizing process, a crystallization of the resin is progressed due to the stretched condition of the resin film, resulting in a strong orientation of the polymer chain, thereby increasing the rigidity of the film. Thanks to the increased rigidity of the polyethylene film constructing the bag in the present invention, the base member is prevented from being collapsed during the infusion process, so that the opposed surfaces of the bag cannot be brought to a closely contacted condition until the liquid infusion is substantially completed. As a result, a desired displaying ability of the liquid surface is maintained at a considerably progressed condition of the liquid infusion operation.

In the present invention, the bag constructing the liquid infusion container is formed as a standing bag, on one hand and, on the other hand, a suspension to an infusion stand is done in a manner that the base member is located at the top. The portion of the bag to be suspended to the infusion stand is located on one side of the bag, i.e., an extended part from its skirt part. At the opposite side, the surface of the bag includes printed marks for indicating respective residual volumes, thereby obtaining a desired visibility of the residual volumes.

BRIEF EXPLANATION OF DRAWINGS

FIG. 11 illustrates an infusion container according to the present invention of fully charged volume of 500 mL during the liquid, (A) illustrating a plan view, (B) illustrating a side view.

FIG. 12 in (A) and (B) is similar to FIG. 11 but illustrates a condition of a residual volume of 400 mL.

FORMS FOR PRACTICING THE INVENTION

The present invention will, now, be explained with reference to an embodiment, wherein a bag with a base member is formed from a soft raw sheet of film, such as blown extruded film, having a doubled part of a gusset shape. In place of such a gusset raw sheet, a normal flat raw film sheet may be used. From the flat sheet, a section, that becomes base member in the successive sticking process, is subjected to cutting. The inventor has no intension to exclude such a possibility from the breadth of the present invention. As to the formation of a bag from the blowing extruding film sheet, see, for example, Japanese Un-Examined Japanese Patent Publication No. H2-92529.

Figure 1:
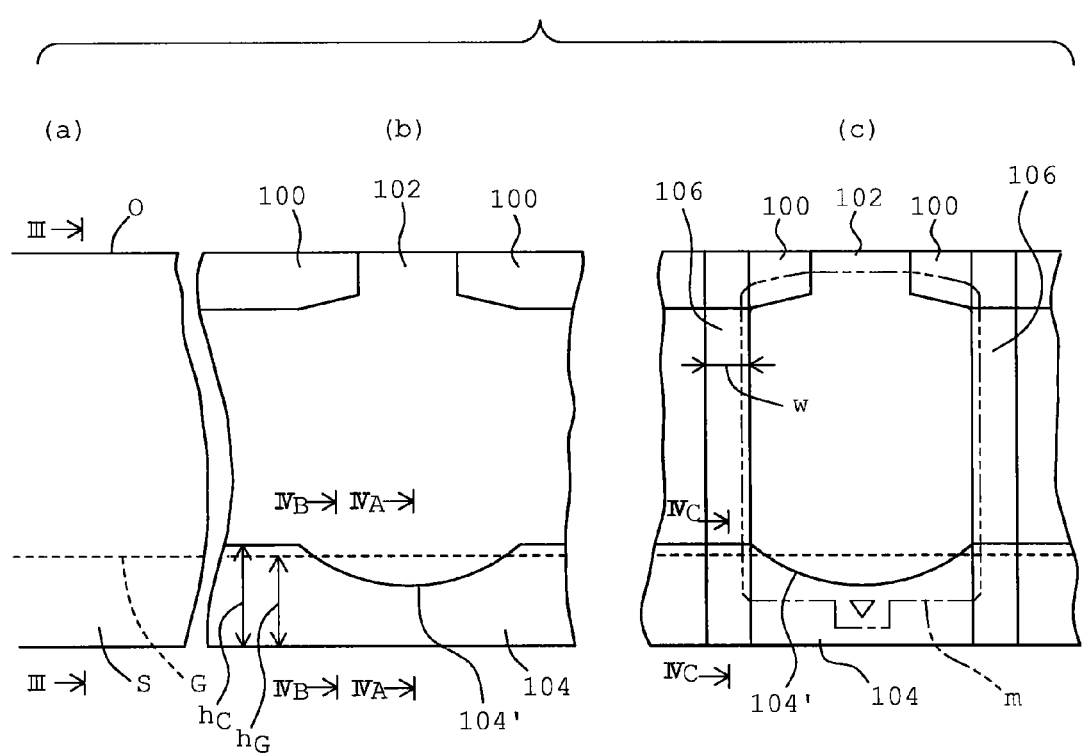
FIG. 1 illustrates steps (a)-(c) for forming a bag of an infusion container.
Figure 2:
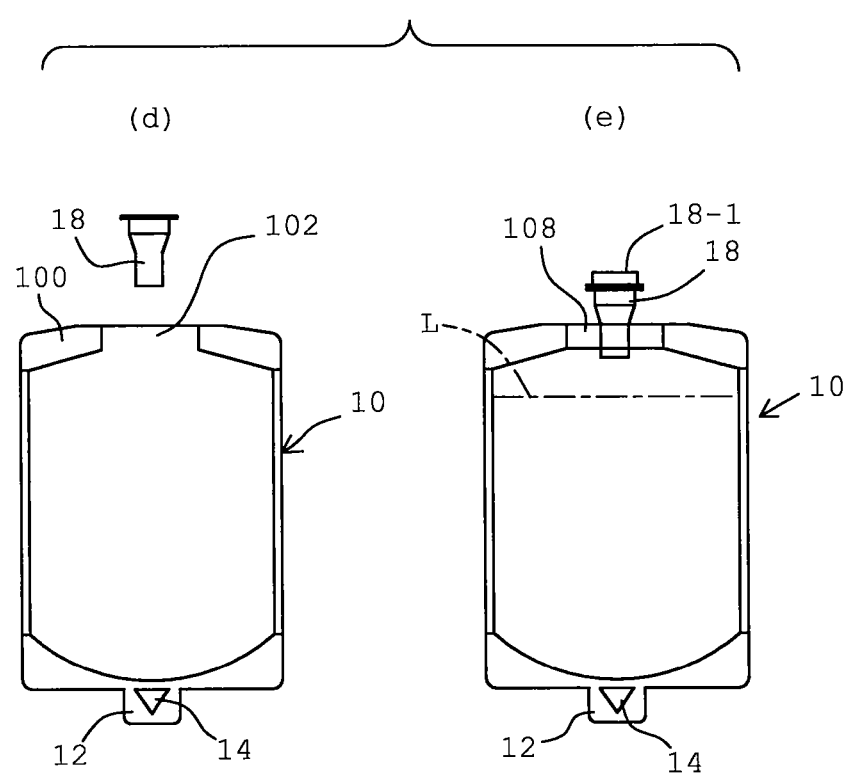
FIG. 2 illustrates steps (d) and (e) following to those in FIG. 1.
Figure 3:
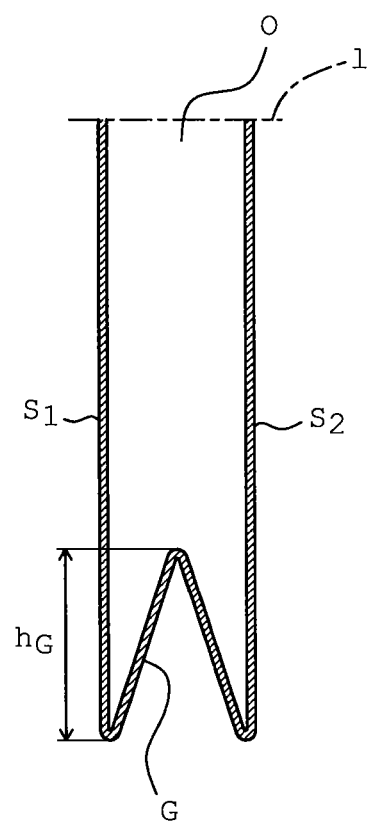
FIG. 3 is a schematic cross-sectional view of a gusset sheet (film thickness is shown exaggerated) prior to the welding, taken along lines III-III in FIG. 1.

FIGS. 1 and 2(*a*) to (*d*) illustrate schematically stages for a production of a standing bag type infusion liquid container according to the present invention. A sheet S (a raw sheet) as blown extruded soft film made of a resin such as polyethylene is made flat and is fed under a sheet condition (FIG. 1(*a*)). FIG. 3 illustrates a sheet taken out from a roll at its half part along the longitudinal axis l and upper and lower polyethylene films constructing the sheet S is illustrated by S1 and S2, respectively. The sheet is cut into two halves along the centerline l in the direction of feed and the cut portion becomes an opening O. As described in the Patent Document 1, the cut of the bag into two halves along the centerline l is usually done after the welding along the profile of the bag, i.e., a pair of bags are formed astride the centerline l. In the following explanation, it is presumed that a cutting of the bag into the two halves has already been done for the sake of the convenience.

In the present invention, the thickness of the film in case of the polyethylene film is in a range between 180 and 350 µm, preferably in a range between 220 and 320 µm. In FIGS. 1 to 9, the thickness is, however, illustrated in an exaggerated manner for the sake of the clarification of the construction of the infusion liquid container according to the present invention. In FIG. 3, the double sheet S is, at a closed end, in advance, inwardly folded, so as to form a gusset portion G, which gusset portion G becomes a base member when a standing bag type infusion liquid container is formed.

Figure 4A:
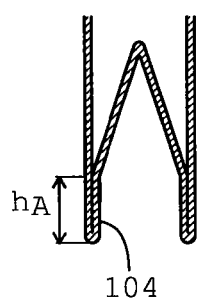
FIG. 4 is schematic cross-sectional views of a gusset sheet (film thickness is shown exaggerated) after the welding, (A) being taken along lines IVA-IVA in FIG. 1, (B) being taken along lines IVB-IVB in FIG. 1, (C) being taken along lines IVC-IVC in FIG. 1.
Figure 4B:
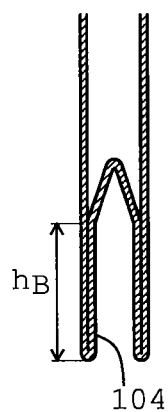
Figure 4C:
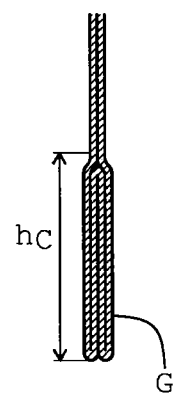

FIG. 1(*b*) illustrates a welding process of the doubled sheet S at the side (upper side of FIG. 1) which becomes the opening O of the sheet S (See FIG. 3) and the side (lower side of FIG. 1) where the gusset part G is located. Namely, at the upper side of the doubled sheet S, i.e., at the side where the opening O is located, the opposed films are welded along the length of the sheet. The welded parts are illustrated by reference numerals 100. The welding temperature is about 130 in case of the polyethylene sheet and the opposite films are non-separably welded. Spaced along the length are portions 102, which are kept non-welded. As will be described later, a connection of an outlet port or a spout is done at the non-welded portion 102. On the lower side of the doubled sheet S, i.e., the side of the sheet where the gusset G is located, the opposed film parts are, at the both sides of the sheet S, as shown in FIGS. 4 (A) and (B), non-separably welded under the same temperature condition, while the inwardly folded part being left un-welded. In FIG. 1(*b*), a line 104' illustrates how the height of the weld portion changes along the sheet length. The weld height is small (weld height of $h_A$) at the portion of the bag as a center part of an infusion liquid container, as shown in FIG. 4(B). As closer to the side portion of the bag, higher is the weld height (weld height of $h_B$). In this way, it is possible to form a bottom of an infusion liquid container such that the bottom has a reduced height at its center portion and an increased height as located closer to the side portion.

FIG. 1(*c*) illustrates the next stage. As spaced along the length of the sheet S, portions 106 of the sheet, each extending along the entire vertical width, are welded, so that portions, which become side parts of bags, are formed. FIG. 4(*c*) illustrates this weld structure, wherein the four film sections are integrated at the height of the gusset portion G, i.e., the lower side of FIG. 4(*c*) and two film sections are integrated at the height above the gusset portion G. The line 104', which becomes the height of the bottom of the bag, exceeds the inwardly bent height $h_G$ at the location of the sheet, which becomes the sides of the bag, resulting in a reinforcement of the bottom of a bag as formed. Furthermore, the non-separable welding at the parts 106 extends along the width w and the welding condition thereat is the same as the welding condition at the parts 100 and 104. Then, a bag(s) is obtained from the sheet S by a cutting and trimming. Namely, in FIG. 1(*c*), a two-dot chain line m illustrates a borderline of a bag and a cutting of the sheet along the line m allows a bag 10 to be obtained as shown in FIG. 2(*d*). A trimming of the bag is, then, done in a manner that a tongue portion 12 is left on one welded side in the gusset portion G. Furthermore, the tongue portion 12 is formed with an opening 14 for suspending purpose. As shown in FIG. 2, the welded part 100 is interrupted at the location 102, which becomes an opening for connection of an outlet port 18 in an infusion liquid container.

A filling process is carried out in a conventional manner. Namely, the bag 10 is held while the opening 102 is located above (See FIG. 2(*d*)). An outlet port (spout) 18 is, without being connected to a cap part 18-1, situated in the opening 102 (See FIG. 2(*e*)). An upper and lower film sections constructing the opening 102 are non-separably welded to the outlet port (spout) 18 for connecting the outlet port to the bag 10. An introduction of a predetermined volume of an infusion liquid is done, which is followed by a tight sealing of the outlet port 18, i.e., a sealing by a connection of the cap part 18-1 and a rubber plug 22 in FIG. 6, while leaving an air space of a volume of around 100 cc, thereby finishing as an infusion liquid container (See FIG. 4(*e*). After filling the infusion liquid followed by the sealing of the bag 10, the latter is subjected to a sterilizing operation under a wet heat condition. A cooling necessarily occurring after the completion of the wet heated sterilizing operation causes a polymeric crystallization to be generated in the resin films constructing the bag 10, resulting in an increase in the rigidity of the bag 10, which rigidity increase contributes to a collapsing characteristic of the bag as intended. In more detail, the sterilizing operation is done by storing in a furnace an infusion liquid container constructed by a bag storing therein with the predetermined volume of the infusion liquid. The wet heated sterilization is executed at a temperature suitably exceeding 100° C. to so as to obtain a steam, resulting in an increase in the pressure inside the bag 10. The increased pressure together with the volume of the air of as large as about 100 cc causes the resin film constructing the bag 10 to be fully inflated. Note: It is necessary to control the pressure outside the bag 10 in the furnace for preventing the bag from being burst. The inflation of the bag 10 causes the resin films constructing the bag 10 to be stretched. In addition, a progress of the cooling after completion of the sterilization serves to promote the crystallization of the resin film as in the stretched condition, which leads to an increase in the rigidity of the resin film.

Figure 5:
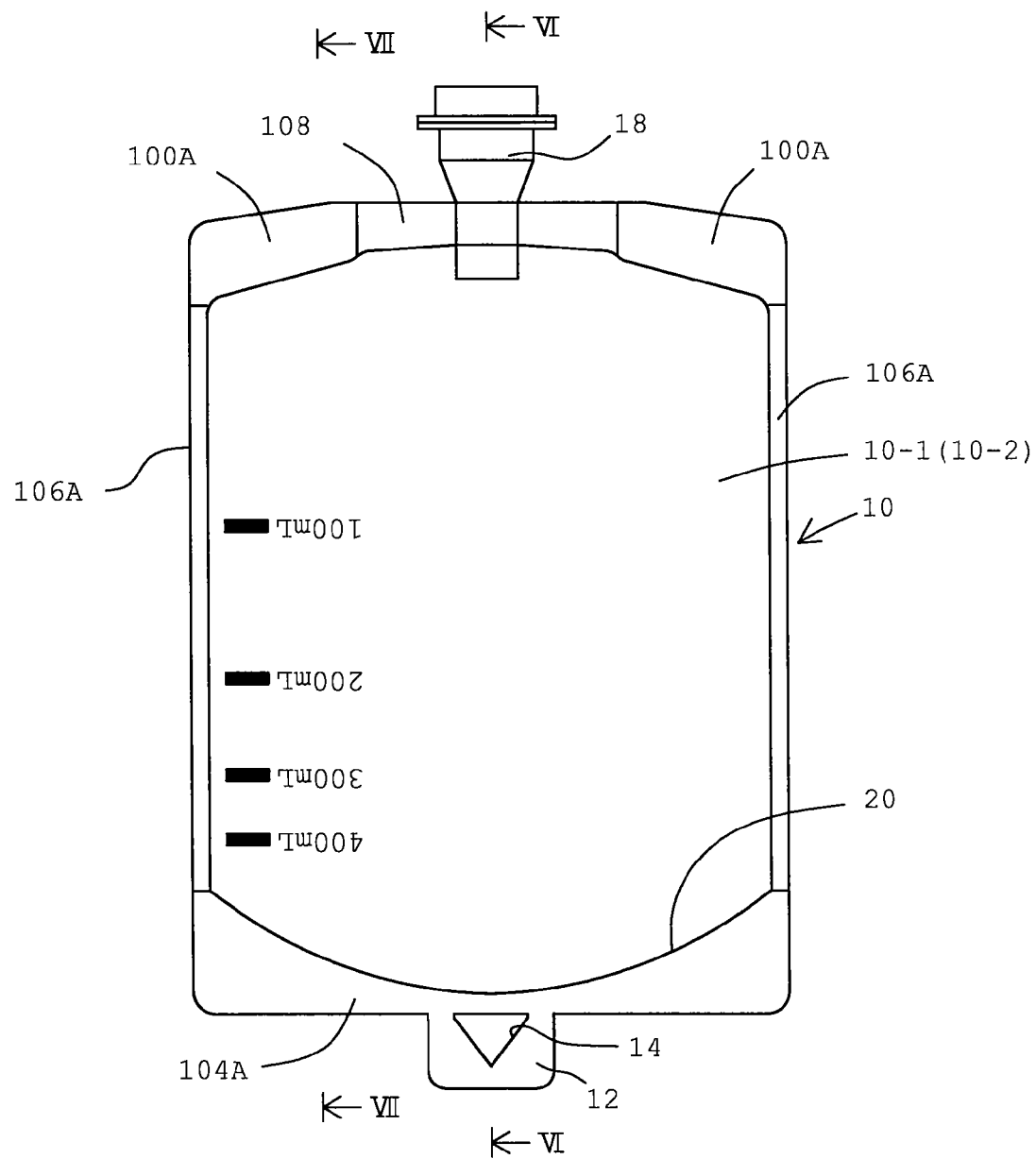
FIG. 5 is a plan view of an infusion container according to the present invention.
Figure 6:
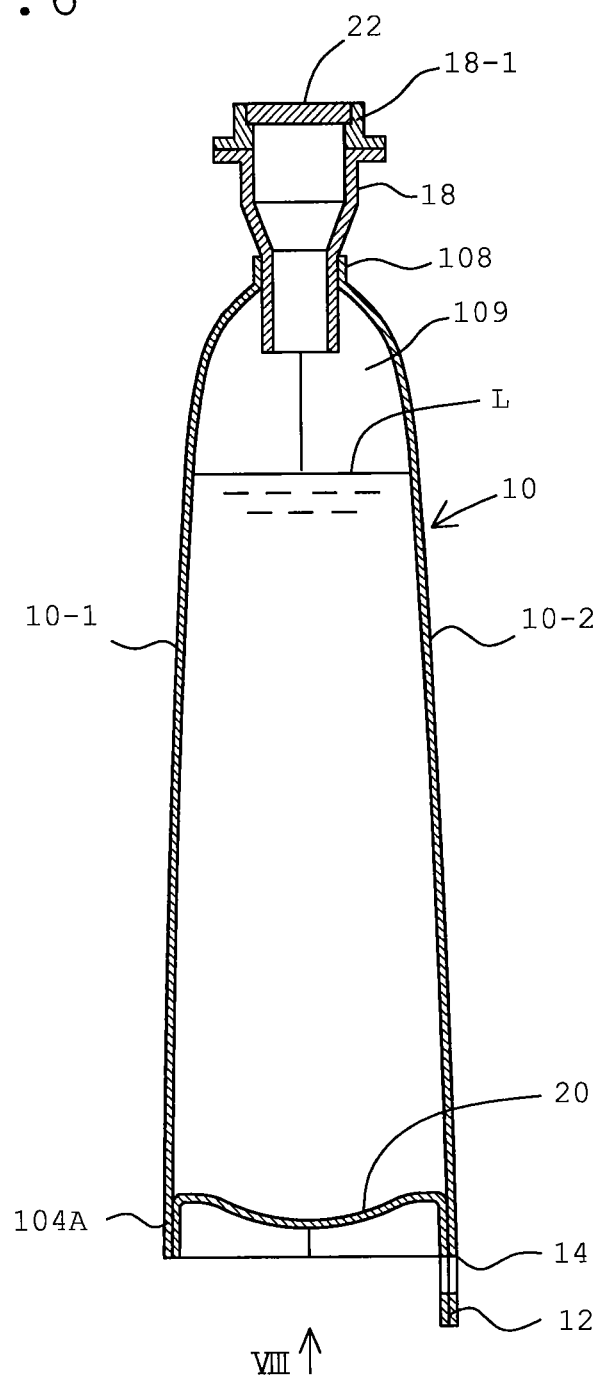
FIG. 6 is a schematic cross-sectional view (film thickness is shown exaggerated) taken along lines VI-VI in FIG. 5.
Figure 7:
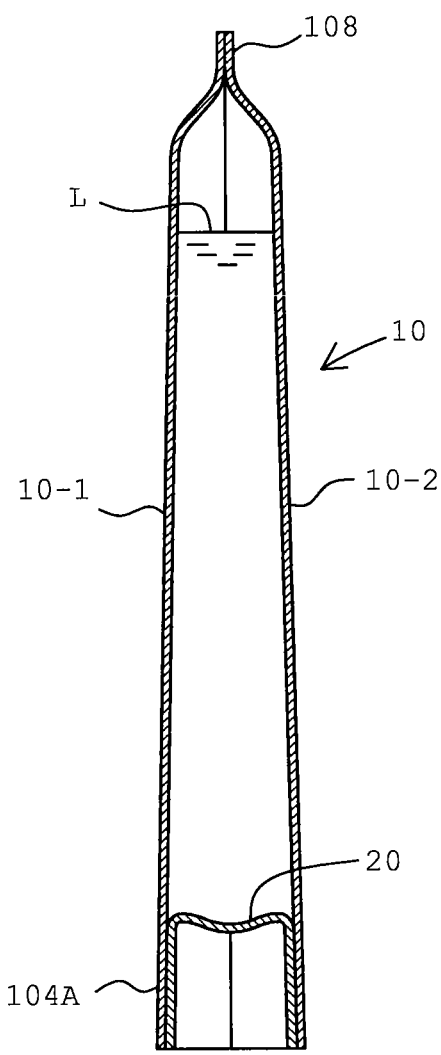
FIG. 7 is a schematic cross-sectional view (film thickness is shown exaggerated) taken along lines VII-VII in FIG. 5.
Figure 8:
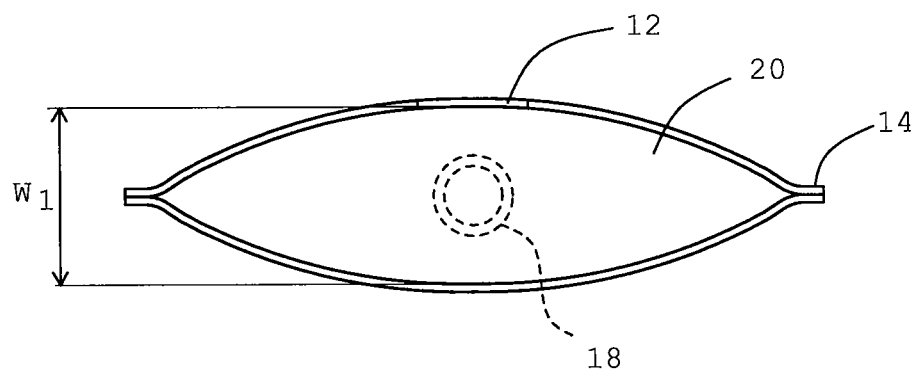
FIG. 8 is a schematic bottom view of the infusion container (film thickness is shown exaggerated) according to the present invention taken along a line VIII in FIG. 6.

FIGS. 5 to 8 illustrates a standing bag type infusion liquid container as a finished product filled therein with an infusion liquid and subjected already to a sterilizing operation, while being under the upright condition. Note that the maximum value of film thickness is 350 µm in the present invention. FIGS. 6 to 8 show however fairly exaggerated film thickness over the actual ones for the sake of a clarification of the structure. In FIG. 6, a line L illustrates the level of the stored infusion liquid. An air chamber above the liquid level L is designated by a reference numeral 109 and is of a volume about 100 cc. The infusion liquid container is provided with a bag 10 and an outlet port 18. The bag 10 is constructed by opposed films 10-1 and 10-2, which correspond, respectively, to sheet parts S1 and S2 in FIG. 3 and which are non-separably welded entirely peripherally at the parts 100A, 104A and 106A, corresponding to welded parts 100, 104 and 106, respectively in FIG. 1 and at the part 108 (FIG.

Figure 9:
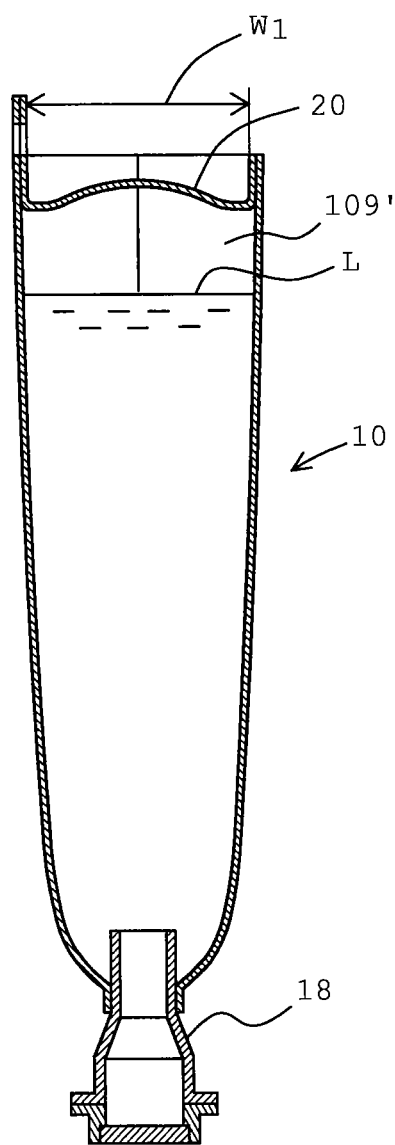
FIG. 9 shows the infusion container with a base member in FIG. 6 at its reversed condition where the base member is located at the top.
Figure 10:
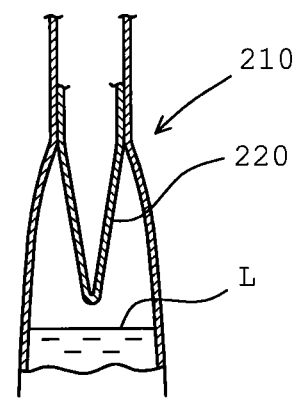
FIG. 10 shows, partly, an infusion container with a base member in a prior art at its reversed condition where the base member is located at the top and illustrates schematically how the base member is collapsed.

2). The bag 10 has a base member 20, which is constructed from the gusset part G (FIG. 3) of the raw film sheet S as subjected to the welding as shown in FIGS. 4(A), (B) and (C) and trimmed as shown in FIG. 1(c). In FIG. 6, the base member 20 is formed from a strip or plate shape functioning as a strut for keeping a widened state of the bag at its one end. The base member 20 serves the infusion liquid to keep the standing position. The welded parts 104A function as skirt part in the standing arrangement. In the gusset part G of the raw film sheet S, the welding height is the maximum at the center part and becomes lower as closer to the both side parts. In the standing condition, the base member 20 as viewed from the front side in FIG. 5 has, therefore, a curved shape, which has the lowest height at the center and the larger height as closer the sides. Furthermore, the base member has a shape as viewed from the lower side as in FIG. 8 such that it has the largest width at the central part and has the narrower width as located closer to the side portions. The weight of the infusion liquid generates a force in the base member 20, which urges the latter to be bent. Apart from this, according to the present invention, the base member 20 can maintain its curved shape even under the absence of the weight of the infusion liquid. Namely, FIG. 9 illustrates the infusion liquid container in an upside down condition, i.e., a state of the latter suspended by an infusion stand, wherein the base member 20 is located at the top. Note: FIG. 9 is exaggerated so long as the film thickness is concerned in a similar way to FIG. 6. As a result of the upside down arrangement, the base member 20 is free from the weight of the infusion liquid and the liquid level is illustrated by the line L. An air space below the base member 20 is illustrated by a reference numeral 109'. An increased rigidity of the resin film constructing the bag 10 according to the present invention serves to fix the shape of the base member 20 although a trace of the folded part in the raw gusset film is more or less left. In short, the maximum wideness $W_1$ of the base member 20 at the middle as shown in FIG. 8 is kept unchanged or substantially unchanged over that at the standing state in FIG. 6 and any collapse of the base member 20 does not occur irrespective of the progress of the liquid discharge process. In other words, the base member 20 or the portion of the bag including the base member 20 is prevented from being subjected to the collapsing. FIG. 10 shows schematically a conventional infusion liquid container as in Patent Document 1 or Patent Document 2 et al, which is, from a standing condition, reversed so that a base member 220 of the bag 210 constructing the container is located on the top. In the standing condition, whereat the weight of the infusion liquid is applied to the base member as is also in the present invention as shown in FIG. 6, so that the base member forms a stretched or downwardly curved shape. A reversing from the standing condition however makes the base member of the bag free from the weight of the infusion liquid container, which causes the base member 220 to assume, instantly, a folded shape as shown in FIG. 10 due to the low rigidity of the resin film, i.e., the base member 220 to be collapsed. Furthermore, the progress of the discharge of the infusion liquid is obtained due to the fact that the bag is entirely flatly collapsed.

In the standing arrangement of the infusion liquid container as shown in FIG. 6, the outlet port 18 is located at the top. The outlet port 18 is a molded product of a tubular shape of polyethylene material and of rigidity, i.e., thickness capable of keeping the tubular shape. A rubber plug 22 is provided at the top for closing the outlet port 18 and is capable of pierced by an infusion set during the infusion operation as will be explained later. A sealing of the outlet port 18 to the bag 10 is obtained by the welding part 108.

The film side 10-2 on one side of the bag 10 is provided with a tongue part 12 (FIG. 5) as obtained by trimming the welded part on one side of the gusset portion G of the raw film S as illustrated in reference to FIG. 1(C). The tongue film 12 is formed with an opening 14 functioning as a suspending member (suspending means), which allows the bag to be suspended by an infusion stand. FIG. 6 shows the thickness of the film in an exaggerated manner. The film thickness is, at the maximum, of value of 350 μm, which makes the film to be soft to be easily flexed when the infusion liquid container is brought into a standing position. In other words, the presence of the tongue part 12 does not provide any cause of trouble for obtaining a standing position of the infusion liquid container at the base member 20. On the film side 10-1 opposite the film side 10-2 on which the opening 14 is formed, marks for an indicative of residual liquid volumes of 400 mL, 300 mL, 200 mL and 100 mL, respectively are printed. In the present invention, an infusion operation is done at an arrangement of the base member 20 at the top. These residual liquid markings are, therefore, looked vertically reversed as shown in FIG. 5 when the container is made to be stand-up by the base member 20 at the lower side.

FIGS. 11 to 14, each as a combination of a front and side views, illustrate an infusion liquid container of a designated volume of 500 mL according to the present invention at residual liquid volumes of 500 mL, 400 mL, 200 mL and 0 mL, respectively during a liquid discharging test. Inside the infusion liquid container, an air space 109' is located on the side of the base member 20. In case where the infusion liquid includes any pharmaceutical unstable to the oxygen, a suitable amount of an inert gas such as nitrogen may be mixed. Furthermore, in FIGS. 11(B) to 14(B), the polyethylene film constructing the bag illustrated by a film thickness near the actual thickness of 250 μm in the embodiment unlike FIGS. 5 to 8. In these drawings, the polyethylene film is, therefore, depicted non-distinctively so long as the film thickness is concerned.

For executing a liquid discharge test, the bag 10 is, at the opening 14 in the tongue portion 12, engaged with a L-shaped hook 24, so that the infusion liquid container assumes a suspended condition where the outlet port 18 is located at the bottom. The suspended condition causes the base plate 20 to be free, so that the latter is prevented from being applied to the weight of the infusion liquid. Irrespective of the freeing of the base member 20 from the liquid weight, the width $W_1$ of the base member 20 is unchanged over that in the standing condition as already explained with reference to the schematic view of FIG. 9. As a result, the base member 20 retains a slightly upwardly convex shape as shown in a dotted line in FIG. 11(B). In the suspended condition, the bag 10 has a portion 10A of a height H from the top edge of the bag 10 of the largest transverse width, which portion 10A is referred hereafter as a bag shape retainer (retaining) part. Below the bag shape retainer part 10A, a body part 10B and a neck part 10C of gradually reduced transverse width continues and finally leads to the outlet port 18. A needle 30A of an infusion set is pierced to the rubber plug 22 (FIG. 6) of the outlet port 18. A preparation of a liquid discharge test is thus completed. In the fully charged condition, $L_{500}$ illustrates a liquid level, above which an air space 109 of a volume of 100 cc is left.

Figure 13A:
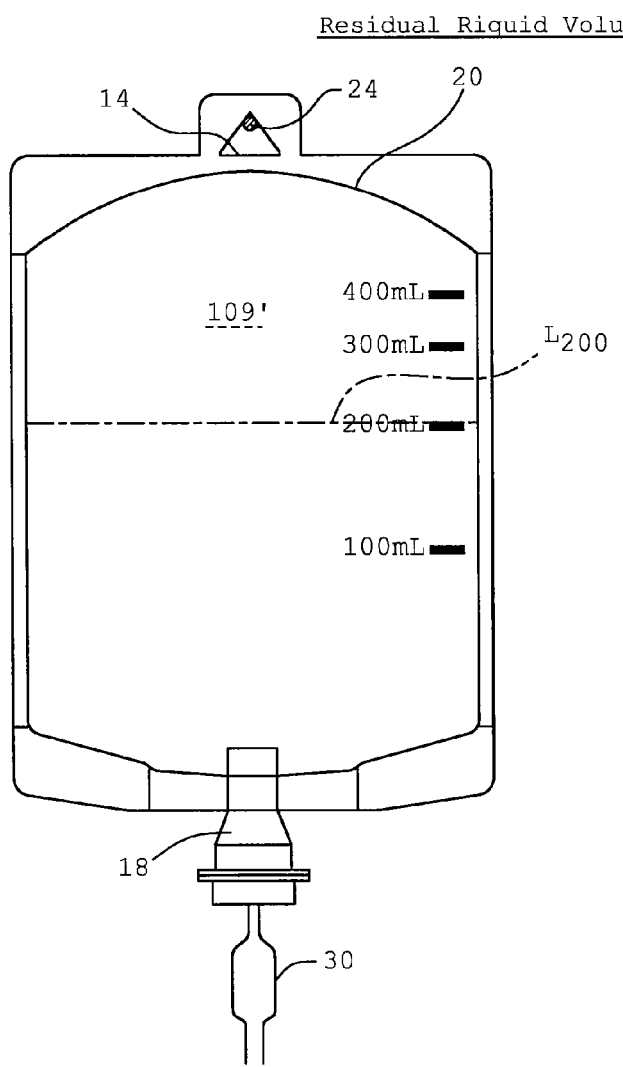
FIG. 13 in (A) and (B) is also similar to FIG. 11 but illustrates a condition of a residual volume of 200 mL.
Figure 13B:
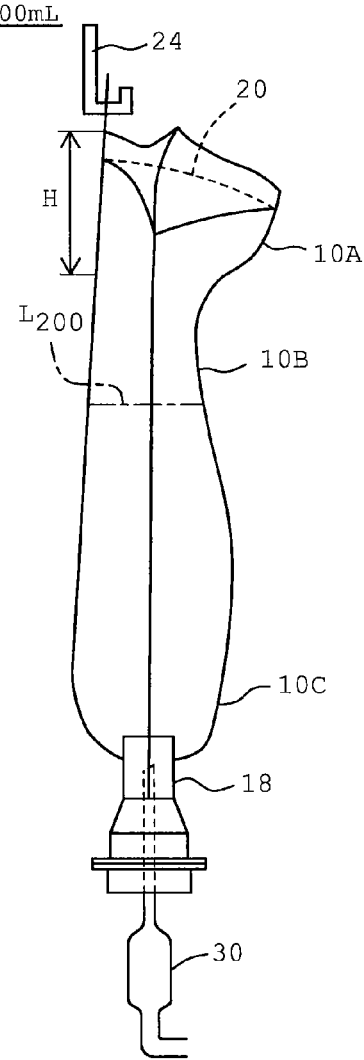
Figure 14A:
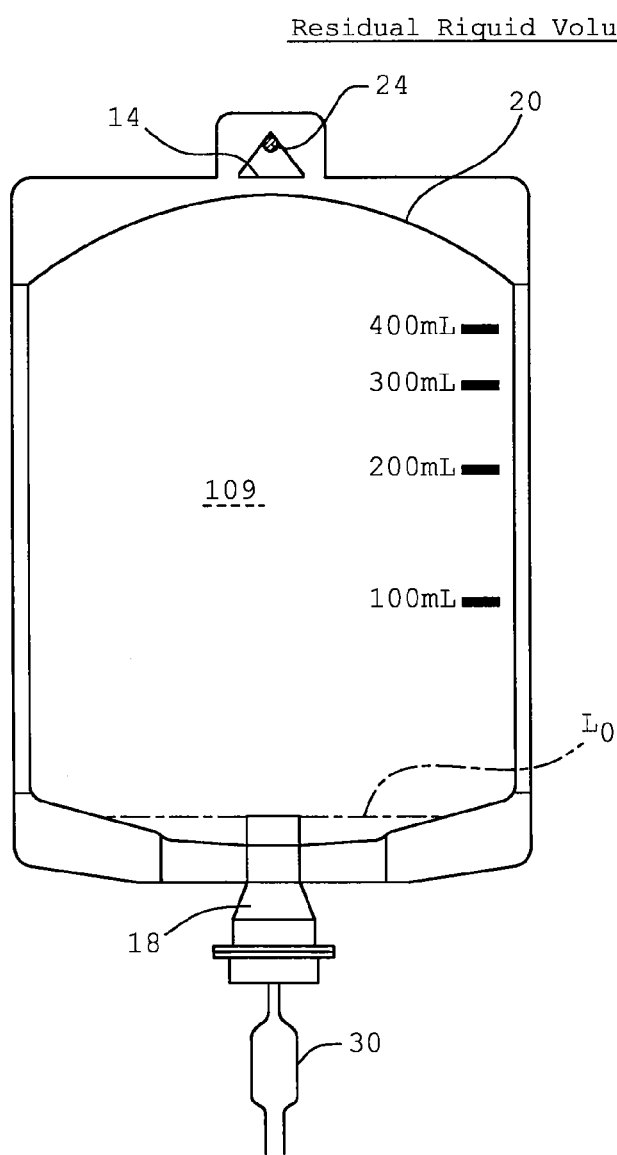
FIG. 14 in (A) and (B) illustrates a condition of a residual volume of 0 mL.
Figure 14B:
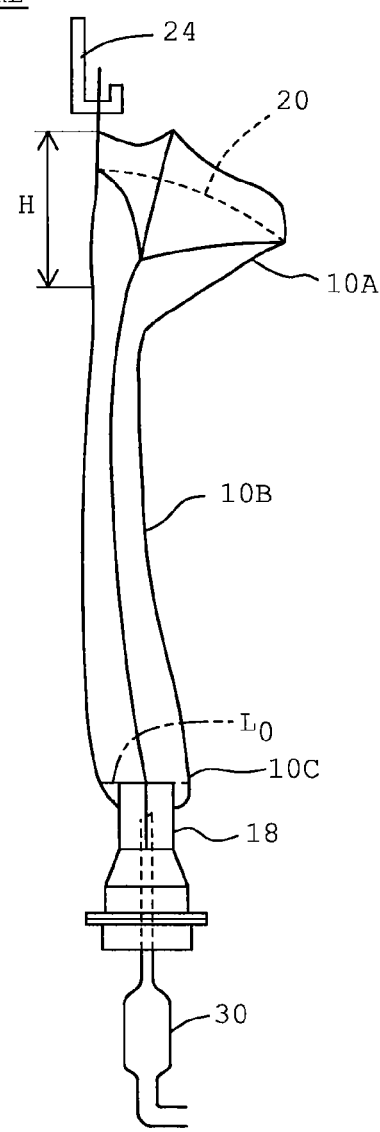

Even the progress of the liquid discharge process as represented by the residual liquid volume of 400 mL and 200 mL, the high rigidity of the films constructing the bag serves to maintain the width of the base member 20. As a result, any collapse of the bag shape retainer part 10A of the height H from the top edge of the bag does not occur or does not substantially occur. As to the body part 10B connected to the bag shape retainer part 10A, the high rigidity of the films constructing the bag serves suitably control the progress of its collapse as shown in FIGS. 12 and 13. As a result, a suitable gap is left between the opposed films and prevents the opposed films from being contacted, so that a desired indication of the liquid level as shown by dotted line $L_{400}$ or $L_{200}$ is obtained. FIG. 14 illustrates a condition of a liquid residual volume of 0 mL. In this condition, the liquid level $L_0$ flushes with the open end of the outlet port 18, thereby preventing the liquid flow from being continued. In this condition, the bag shape retaining part 10A is still prevented from being collapse or from being substantially collapsed. Although collapses of the body part 10B as well as the neck part 100 are progressed, the gap between the opposed films is maintained, which opposed films are, therefore, prevented from being contacted with each other, thereby obtaining an accurate indication of the residual volume up to 0 mL. The changes of the cross-sectional shape of the body part 10B and the neck part 100 of the bag 10 as shown in FIGS. 11(B) to 14(B) as a result of the progress of the discharge of the liquid necessarily cause the front shape of the bag as shown in FIGS. 11(A) to 14(A) to be correspondingly and slightly changed. The degree of changes of the front shape of the bag is not so remarkable and is not related to the gist of the invention. In FIGS. 11(A) to 14(A), the front shapes of the bag are therefore shown identically except the varied positions of the liquid level.

Now, a rigidity of the polyethylene film constructing the bag for obtaining a shape retaining function of the shape retaining part 10A during the execution of an infusion process will now be explained. The infusion liquid container in the present invention is subjected to a sterilizing operation while a desired volume of the infusion liquid is stored therein. During a cooling occurred after the execution of the high temperature sterilization, a crystallization of the polyethylene polymers is promoted, resulting in an increased rigidity of polyethylene films larger than that of the raw materials. The rigidity of the polyethylene film as expressed by 1% elastic modulus intension in a rage between 150 and 320 Mpa, preferably 170 and 280 Mpa. The rigidity in cooperation with the thickness of the film serves to obtain an increased rigidity of the polyethylene film in the stored condition of the infusion liquid. In the shape retaining part 10A, the base member 20 maintains its width and functions as a strut for obtaining a desirably increased shape retaining ability of the shape retaining part 10A. As a result, the shape retaining part 10A maintains its shape and is prevented from being collapsed. Furthermore, collapses of the continuing body part 10B and the neck part 10 continued from the shape retainer part 10A are desirably controlled. As a result, any contact between the opposed films is prevented until a zero residual liquid volume is obtained, thereby keeping a desired ability for making the residual volume to be precisely visible. In case where the bag is formed from a gusset film (FIG. 2) as in this embodiment of the present invention, the base member 20 maintains slightly creased shape even in the stored condition of the infusion liquid. The cooling followed by the sterilization operation at a high temperature promotes the crystallization of the polyethylene high polymer, so that the crease is disappeared or substantially disappeared as shown in FIGS. 11 to 14. Thanks to the shape fixing by the high rigidity, the strut function of the base member 20 is maintained, thereby preventing the shape retaining part 10A from being substantially collapsed irrespective of the progress of the liquid discharge and preventing the liquid level display function from being lost in the infusion liquid container according to the present invention.

As to the thickness of the polyethylene film in the raw sheet condition prior to the bag formation as well as the sterilizing operation, there is no upper limit so long as the function for preventing a collapse is concerned. From the viewpoint of the material cost, the thickness of the polyethylene film has an upper limit of around 350 μm. There is also no lowest limit as far as the collapsing function is concerned. An excessively thin film thickness causes, however, the standing ability to be lost and, in this sense, the lowest value of the thickness is 180 μm and is preferably thicker than 220 μm from the viewpoint of the standing ability.

In addition, the width W1 of the base member in FIG. 8 is in a range between 20 and 45 mm, preferably between 25 and 35 mm, which is effective for obtaining a self standing angle of 10 degree or larger in a stored volume in a range between 150 to 700 mL, preferably between 200 and 500 mL.

Example 1

A polyethylene film of a thickness of 250 μm constructed by three layers of a surface layer of thickness of 20 μm, a middle layer of thickness of 210 μm and an inner layer of a thickness of 20 μm was gusseted, then was welded along a profile of a bag at a temperature of 130° C. so as to form welded portions and finally was cut for obtaining a bag of a height of 200 mm, a lateral width of 140 mm and of bottom width of 40 mm corresponding to $W_1$ in FIG. 8. Then, an infusion liquid of a volume of 500 mL was introduced into the bag and an outlet port 18 was attached and then welded to the bag, while forming an air space of 100 cc above the liquid level, so that an infusion liquid container as shown in FIGS. 5 to 8 was produced. Then, the infusion liquid container was subjected to a sterilizing process under a wet heat condition in a furnace at a temperature of 111° C. and of a heating time of 20 minutes. From various polyethylene material samples of values of specific weight of 0.898 to 0.945 provided by various producers, 2 to 5 samples of suitable values of specific weight and basically of the one and the same producer were selected and were mixed at respective mixing rates, so that fifteen different types of bags from No. 1 to No. 15 in the Table 1 were constructed. Values of 1% elastic modulus in tension of each of three layer polyethylene films constructing No. 1 to No. 15 bags after subjected to the sterilization operation were measured. Furthermore, each of the infusion liquid containers constructed from the respective bag was at its opening 14 in the respective tongue part 12 suspended by L-shaped member 24 as illustrated in FIGS. 11 to 14 and was subjected to a liquid discharge test for an evaluation of a liquid discharging performance as well as a shape of the base member 20, i.e., the shape retaining part 10A.

TABLE 1

| Sample No. | Stretch Modulus (Mpa) | Discharge-Ability & Shape of Base Member |
|---|---|---|
| 1 | 173 | ○ |
| 2 | 140 | Δ |
| 3 | 213 | ○ |
| 4 | 193 | ○ |
| 5 | 184 | ○ |
| 6 | 280 | ○ |

TABLE 1-continued

| Sample No. | Stretch Modulus (Mpa) | Discharge-Ability & Shape of Base Member |
|---|---|---|
| 7 | 242 | ○ |
| 8 | 240 | ○ |
| 9 | 207 | ○ |
| 10 | 205 | ○ |
| 11 | 225 | ○ |
| 12 | 170 | ○ |
| 13 | 115 | X |
| 14 | 117 | X |
| 15 | 164 | Δ~○ |

In the above table, the mark ○ represents a result of an evaluation that the residual volume visibility was maintained since the shape retaining part 10A was prevented from being collapsed until the residual volume of 0 mL. The mark Δ represents a result of the evaluation that the residual volume visibility was almost maintained since the shape retaining part 10A was prevented from being collapsed until the last phase of the discharge irrespective of an occurrence of a contact between the faced film surfaces at the last phase of the liquid discharge of the residual liquid volume below 100 mL. The mark x represents a result of an evaluation that the residual volume visibility is insufficient since a collapse of the shape retaining part 10A was occurred at an earlier stage of the liquid discharge of an increased volume of the residual liquid volume.

Example 2

An infusion liquid container of standing bag type made of polyethylene a film, of the height of 140 mm and of bottom width of 40 mm for storing a liquid volume of 200 mL as similar to that in Example 1 was produced. The conditions for producing the bag was identical to those in the Example 1 and the residual air volume was also identical, i.e., 100 cc. A result of evaluation of the liquid discharge ability as well as the shape of the shape retaining part as subjected to the liquid discharge test were the same as the result shown in the Table 1 in the Example 1.

Example 3

As also to an infusion liquid container of the height of 150 mm, of charged volume of liquid of 250 mL, of the same width and of residual air space volume of 150 cc, a similar result was obtained so long as a liquid discharge ability as well as a shape evaluation of the shape retaining part are concerned.

As a summary, an increased rigidity of a polyethylene film constructing the bag is obtained by subjecting the bag to a sterilizing operation under wet heat condition in a charged condition of a liquid of an volume between 200 and 500 ml while an air gap between 100 cc and 150 cc is provided so that 1% elastic modulus in tension in a rage between 150 and 270 Mpa, preferably between 170 and 240 Mpa is obtained. This arrangement allows the base member as well as a shape retaining part including the base member is prevented from being collapsed. As a result, a desired visibility of the residual liquid volume from the start and the end can be obtained.

BRIEF EXPLANATION OF SOME REFERENCE NUMERALS

10: Bag
10-2, 10-2: Opposed Film Surfaces of Bag
10A: Bug Shape Retaining Part
10B: Barrel Part of Bag
10C: Neck Part of Bag
14: Opened Part
18: Outlet Port
20: Base Member
22: Rubber Plug
26: Air Gap
30: Infusion Set
100, 104, 106, 108: Welded Part
109, 109': Air Gap
G: Gusset Part
S: Raw Film
S1, S2: Polyethylene Film

The invention claimed is:

1. A standing infusion liquid container comprising:
a squeezable bag configured to store therein an infusion liquid, the squeezable bag being a flat pouch of a welded structure formed from film sheets cut from a continuous raw flexible sheet made from a resin material and having a first end configured to function as a base member;
a suspension member configured to suspend the squeezable bag so that the base member is located at a top of the standing infusion liquid container;
an outlet port for the infusion liquid at a second end of the squeezable bag; and
indication marks for a visual indication of a volume of a residual liquid, the indication marks being formed on a surface of the squeezable bag,
wherein the infusion liquid is filled in the squeezable bag such that an air space is left therein and such that the volume of the residual liquid is visible on a liquid level basis relative to the indication marks,
wherein the base member of the squeezable bag, under a suspended condition by the suspension member, has a value of width, which is equal to a value of the width of the base member under a standing condition of the squeezable bag, and
wherein, in the suspended condition where the squeezable bag is suspended by the suspension member, the base member maintains the value of width without being collapsed regardless of discharge of the infusion liquid, and the base member operates such that opposed sidewalls of the squeezable bag, formed of the film sheets, at any location below the base member are prevented from coming into contact with each other along an entire process of infusion, thereby obtaining a desired indication of gradually reduced level of infusion liquid remaining in the squeezable bag by the indication marks throughout the infusion process.

2. The standing infusion liquid container according to claim 1, wherein a portion of the squeezable bag including the base member in a part of the squeezable bag a predetermined height from the first end of the squeezable bag constructs a shape retainer to retain a width of the part of the squeezable bag by preventing the part of the squeezable bag from being collapsed regardless the discharge of the infusion liquid from the squeezable bag.

3. The standing infusion liquid container according to claim 1, wherein the suspension member is formed as an opening on a first side of the squeezable bag, at the first end, and said indication marks are formed on a second side of the squeezable bag opposite the first side.

4. The standing infusion liquid container according to claim 1,
wherein the resin material for the film sheets constructing the squeezable bag is polyethylene resin,
wherein a raw polyethylene film of the film sheets has a value of thickness in a range between 180 and 350 μm, and
wherein a polyethylene film of the film sheets as constructed to the squeezable bag has a value of 1% elastic modulus in tension in a range between 150 and 320 Mpa.

5. The standing infusion liquid container according to claim 1, wherein an inactive gas is mixed with the air inside the squeezable bag.

6. The standing infusion liquid container according to claim 1, wherein, in a side view of the a squeezable bag, in the suspended condition where the squeezable bag is suspended by the suspension member, the value of the width of the base member is greater than any other width of the squeezable bag below the base member.

7. The standing infusion liquid container according to claim 1, wherein the base member includes a strip or a plate configured to operate as a strut to prevent the opposed sidewalls of the squeezable bag from coming into contact with each other along an entire process of infusion.

8. The standing infusion liquid container according to claim 1, wherein, in a front view of the squeezable bag, in a standing condition where the squeezable bag stands upright via the base member a bottom of the standing infusion liquid container, the base member has a curved shape with a lowest height at a center.

9. The standing infusion liquid container according to claim 1, wherein, in a side view of the squeezable bag, in the suspended condition where the squeezable bag is suspended by the suspension member, the base member has an upwardly convex shape.

* * * * *